(12) United States Patent
Blankenship et al.

(10) Patent No.: US 8,887,575 B2
(45) Date of Patent: Nov. 18, 2014

(54) PRESSURE SENSOR

(71) Applicant: MKS Instruments, Inc., Andover, MA (US)

(72) Inventors: Steven D. Blankenship, Melrose, MA (US); Paul D. Lucas, Melrose, MA (US)

(73) Assignee: MKS Instruments, Inc., Andover, MA (US)

( * ) Notice: Subject to any disclaimer, the term of this patent is extended or adjusted under 35 U.S.C. 154(b) by 138 days.

(21) Appl. No.: 13/649,476

(22) Filed: Oct. 11, 2012

(65) Prior Publication Data

US 2013/0189160 A1 Jul. 25, 2013

Related U.S. Application Data

(60) Provisional application No. 61/545,790, filed on Oct. 11, 2011.

(51) Int. Cl.
*G01L 9/12* (2006.01)
*G01L 19/06* (2006.01)
*G01N 27/22* (2006.01)

(52) U.S. Cl.
CPC .......... *G01N 27/227* (2013.01); *G01L 19/0636* (2013.01); *G01N 9/0075* (2013.01)
USPC .................................. 73/724; 73/715; 73/753

(58) Field of Classification Search
None
See application file for complete search history.

(56) References Cited

U.S. PATENT DOCUMENTS

| | | |
|---|---|---|
| 4,499,773 A | 2/1985 | Crampton et al. |
| 4,785,669 A | 11/1988 | Bensen et al. |
| 4,823,603 A | 4/1989 | Ferran et al. |
| 5,271,277 A | 12/1993 | Pandorf et al. |
| 5,396,803 A * | 3/1995 | Ferran .............................. 73/724 |
| 5,625,152 A | 4/1997 | Pandorf et al. |
| 5,808,206 A | 9/1998 | Pandorf et al. |
| 5,911,162 A | 6/1999 | Denner |
| 5,932,332 A | 8/1999 | Pandorf et al. |
| 5,942,692 A | 8/1999 | Haase et al. |
| 5,965,821 A | 10/1999 | Grudzien |
| 6,029,525 A | 2/2000 | Grudzien |
| 6,105,436 A | 8/2000 | Lischer et al. |
| 6,443,015 B1 | 9/2002 | Poulin et al. |
| 6,464,791 B1 * | 10/2002 | Van de Kerkhof ............ 118/715 |
| 6,568,274 B1 | 5/2003 | Lucas et al. |
| 6,672,171 B2 | 1/2004 | Gu et al. |
| 6,735,845 B2 | 5/2004 | Jonsson |
| 6,901,808 B1 | 6/2005 | Sharpless |

(Continued)

OTHER PUBLICATIONS

International Preliminary Report on Patentability dated Apr. 15, 2014 from Corresponding PCT Application No. PCT/US2012/059697.

*Primary Examiner* — Lisa Caputo
*Assistant Examiner* — Jermaine Jenkins
(74) *Attorney, Agent, or Firm* — McDermott Will & Emery LLP

(57) ABSTRACT

One or more reactive gases are introduced to a capacitance manometer at a particular area or areas of the diaphragm between the inner and outer capacitive electrodes so the error-inducing measurement effects of positive and negative bending are neutralized or minimized. Additionally, a guard structure may be used with the electrode structure of the capacitance manometer. The guard structure presents an area that is relatively insensitive to the diffusion of the gas into the diaphragm and the resulting changing surface tension, thus providing increased or optimal stability of the zero reading of the manometer. The guard may also provide electrostatic isolation of the electrodes.

19 Claims, 12 Drawing Sheets

REACTIVE GAS, E.G., ATOMIC FLUORINE

(56) References Cited

U.S. PATENT DOCUMENTS

| | | |
|---|---|---|
| 6,909,975 B2 | 6/2005 | Dozoretz et al. |
| 6,993,973 B2 | 2/2006 | Lischer |
| 7,000,479 B1 | 2/2006 | Poulin |
| 7,137,301 B2 | 11/2006 | Grudzien |
| 7,155,803 B2 | 1/2007 | Jonsson |
| 7,201,057 B2 | 4/2007 | Agami |
| 7,284,429 B2 | 10/2007 | Chaumet et al. |
| 7,316,163 B2 | 1/2008 | Grudzien |
| 7,389,697 B2 | 6/2008 | Jonsson |
| 7,451,654 B2 | 11/2008 | Maiorana et al. |
| 7,624,643 B2 | 12/2009 | Grudzien |
| 7,706,995 B2 | 4/2010 | Sullivan et al. |
| 7,757,563 B2 | 7/2010 | Grudzien |
| 8,704,538 B2 * | 4/2014 | Grudzien ............ 324/686 |
| 2004/0099061 A1 | 5/2004 | Jonsson |
| 2004/0211262 A1 | 10/2004 | Jonsson |
| 2005/0262946 A1 | 12/2005 | Jonsson |
| 2006/0000289 A1 | 1/2006 | Jonsson |
| 2006/0070447 A1 | 4/2006 | Agami |
| 2007/0023140 A1 | 2/2007 | Grudzien |
| 2009/0255342 A1 | 10/2009 | Grudzien |

* cited by examiner

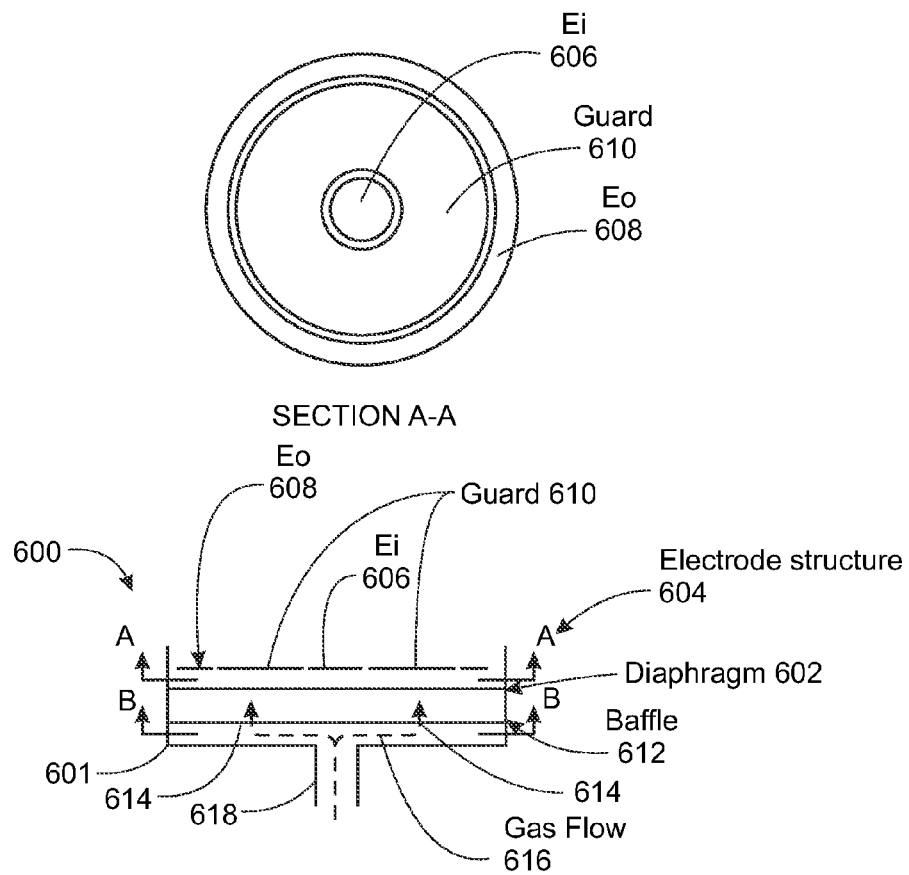
FIG. 6A
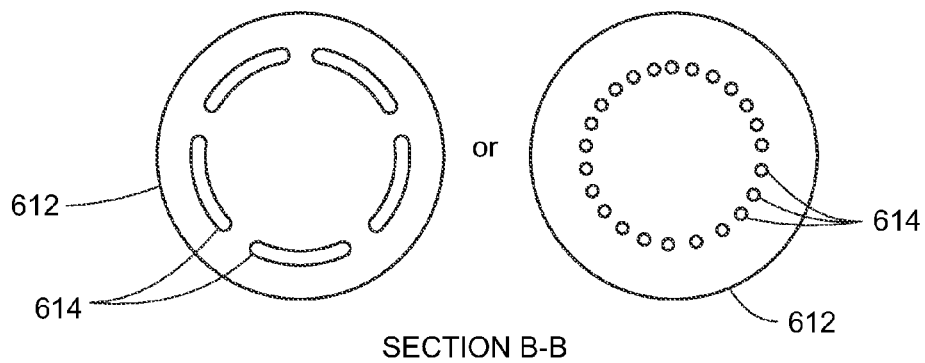
FIG. 6B1        FIG. 6B2

PRESSURE SENSOR

This application claims priority to provisional application No. 61/545,790, filed Oct. 11, 2011, and entitled "Improved Pressure Sensor," the entire content of which is incorporated herein by reference.

FIELD OF THE DISCLOSURE

This disclosure relates generally to a capacitive pressure sensor, and more particularly to an improved sensor providing very precise and accurate measurements of pressure, particularly at very low (vacuum) pressures.

BACKGROUND

Pressure transducers have been employed in a myriad of applications. One such transducer is the capacitive manometer which provides very precise and accurate measurements of pressure of a gas, vapor or other fluid. Applications include precision control of vacuum based processes and semiconductor process control. Examples include semiconductor etch process and physical vapor deposition.

Capacitive manometers typically use (a) a flexible diaphragm forming or including an electrode structure and (b) a fixed electrode structure spaced from the diaphragm so as to establish capacitance there between. Variations in pressure on one side of the diaphragm relative to the pressure on the opposite side of the diaphragm causes the diaphragm to flex so that the capacitance between the electrode structure of the diaphragm and the fixed electrode structure varies as a function of this differential pressure. Usually, the gas or vapor on one side of the diaphragm is at the pressure being measured (Px), while the gas or vapor on the opposite side of the diaphragm is at a known reference pressure (Pr), the latter being at atmosphere or some fixed high or low (vacuum) pressure, so that the pressure on the measuring side of the diaphragm can be determined as a function of the capacitance measurement.

Many applications requiring extremely low pressures (high vacuum) have been and continue to be developed resulting in the need for capacitive manometers capable of measuring such low pressures. Increasing the sensitivity of capacitive manometers to provide very precise and accurate pressure measurements at low pressures, however, poses several design challenges. In order to measure extremely low pressures (high vacuum), a capacitive manometer typically requires a very narrow gap between the flexible diaphragm and the fixed electrode structure (the "electrode gap") so that small changes in pressure can be detected.

A drawback to using a very narrow electrode gap is that smaller changes in the shape of the electrode gap unrelated to the measurement of differential pressure across the diaphragm are also detected. One of these detrimental changes to the electrode gap shape is a change in the shape of the diaphragm by process-related chemical reactions such as the diffusion of gas molecules or atoms into a surface of the diaphragm. Capacitance measurements are based on the well known equation for parallel plate capacitance C:

$$C = e_r e_o A/s, \quad (EQ. 1)$$

where C is the capacitance between two parallel plates,
$e_o$ is the permittivity of free space,
$e_r$ is the relative permittivity of the material between the plates (for vacuum, $e_r=1$),
A is the common area between the plates, and
s is the spacing between the plates.

Based on this equation, one can derive the relationship that the fractional change in capacitance is equal to the negative of the fractional change in electrode gap spacing for each measuring electrode ($\Delta C/C = -\Delta S/S$).

It can be readily seen that it is critical to maintain good control over the electrode gap spacing in order to provide stable control over the capacitance of each measuring electrode. In a simple dual electrode design, these effects are balanced to a first order at zero differential pressure for a flat diaphragm and electrode structure (each having different real values of flatness and inclination deviation from true plane) for a given electrical measurement technique such as with any number of commonly used bridge designs (e.g., the Wheatstone bridge, etc.) and/or other electrical measuring methods. Since the sensor is configured to measure extremely low pressures (extremely small diaphragm deflections), just balancing the electrodes without making a stable electrode gap is not enough to reduce the uncertainty of the pressure measurement to adequately low levels in order to accomplish stable detection of the smallest pressures.

As the capacitive measurements are designed to detect changes in displacement between the fixed electrode structure and the diaphragm pressure resisting element, one source of error relates to any changes in the shape and position of the diaphragm (as it affects the electrode gap), which can produce changes in the sensor output that are unrelated to pressure.

FIG. 1 is a diagram showing a side and top view in views A and B, respectively, of a portion of a prior art capacitance manometer 100. The device includes a diaphragm 102 spaced apart from an electrode structure 104. The electrode structure 104 includes an inner electrode 106 and an outer electrode 108 separated by a gap 110. As shown in view B, the electrodes can have a circular configuration. When a pressure differential exists between the pressure on both sides of the diaphragm 102, the diaphragm is caused to deflect, as shown by alternate position 102'.

FIG. 2 is a diagram showing side and section views in views A and B, respectively, of a portion of another prior art capacitance manometer 200. The device is similar to the one shown in FIG. 1 and includes a housing 201 with a diaphragm 202 spaced apart from an electrode structure 204. The electrode structure 204 includes an inner electrode 206 and an outer electrode 208 separated by a gap 210. The housing includes an inlet 212 for admitting gas to the region adjacent the diaphragm 202. A baffle 214 is present to control entry of the gas to the region adjacent the diaphragm 202. As shown in view B, the baffle may be secured to the housing 201 by multiple tethers 218. The baffle 214 has a solid shape with no interior features. In operation, gas from the inlet 212 goes around the baffle 214 and reaches the outer edge of the diaphragm first 202. The gas then spreads toward the center of the diaphragm 202.

FIG. 3 is a diagram showing side and alternate section views, in A-C, respectively, of a portion of a further prior art capacitance manometer 300. The device is similar to the one shown in FIG. 2 and includes a housing 301 with a diaphragm 302 spaced apart from an electrode structure 304. The electrode structure 304 includes an inner electrode 306 and an outer electrode 308 separated by a gap 310. The housing 301 includes an inlet 312 for admitting gas to the region adjacent the diaphragm 302. A baffle 314 is present to control entry of the gas to the region adjacent the diaphragm 302. As shown in view B, the baffle includes multiple apertures 316 distributed in a uniform distribution over all or the majority of the baffle 314. View C shows an alternate configuration of the baffle, with a uniform radial distribution of apertures 316 over all or the majority of the baffle 314.

Reference is made to U.S. Pat. Nos. 7,757,563; 7,706,995; 7,624,643; 7,451,654; 7,389,697; 7,316,163; 7,284,439; 7,201,057; 7,155,803; 7,137,301; 7,000,479; 6,993,973; 6,909,975; 6,901,808, 6,735,845; 6,672,171; 6,568,274; 6,443,015, 6,105,436; 6,029,525; 5,965,821; 5,942,692; 5,932,332; 5,911,162; 5,808,206; 5,625,152; 5,271,277; 4,823,603; 4,785,669 and 4,499,773; and U.S. Patent Published Application Nos. 20090255342; 20070023140; 20060070447; 20060000289; 20050262946; 20040211262; 20040099061; all assigned to the assignee of the present disclosure; the entire content of all of which patents and patent publications are incorporated herein by reference.

While such prior art manometers may be suitable for their intended purpose, they can never the less be prone to transient measurement errors, particularly when used with reactive gases such as atomic fluorine and the like.

SUMMARY

Aspects of the present disclosure address the previously noted problems by providing baffle and/or electrode structures that can reduce and/or block the measurement of transient diaphragm deformation in or for a capacitance manometer due to effects other than pressure.

In accordance with one aspect of the present disclosure, a capacitive manometer or assembly of a capacitive manometer includes:

(a) a diaphragm including a conductive material and (b) an electrode structure including an inner (or, center) electrode and an outer electrode, wherein the diaphragm is movable relative to the electrode structure between (i) a zero position when the pressure on each side of the diaphragm is the same and (ii) a maximum differential position when the maximum measurable differential pressure is applied to the diaphragm, and (b) a baffle with one or more apertures configured to admit gas to a region adjacent to the diaphragm that minimizes effects of surface deformation of the diaphragm due to effects other than pressure on the output of the sensor. The diaphragm, electrode structure, and baffle may be positioned within a suitable housing.

In accordance with another aspect of the present disclosure, a capacitive manometer or assembly of a capacitive manometer includes:

(a) a diaphragm including a conductive material and (b) an electrode structure including an inner (e.g., center) electrode, an outer electrode, and a guard structure disposed between the inner and outer electrodes, wherein the diaphragm is movable relative to the electrode structure between (i) a zero position when the pressure on each side of the diaphragm is the same and (ii) a maximum differential position when the maximum measurable differential pressure is applied to the diaphragm, and (b) a baffle with one or more apertures configured to admit gas to a region adjacent the diaphragm and strategically located in relation to the guard that further minimizes the effects of surface deformation of the diaphragm due to effects other than pressure on the sensor output. The diaphragm, electrode structure, and baffle may be positioned within a suitable housing.

Exemplary embodiments can provide for a capacitive manometer, or pressure sensor, in which the configuration (e.g., shape, location of features, and/or surface finish and treatment, etc.) of the sensor inlet and slot(s) in the baffle balances or facilitates balancing the deleterious effects on the inner and outer electrodes, in time and effect, due to a reactive gas coming into the sensor, and reacting with the diaphragm.

These, as well as other components, steps, features, benefits, and advantages, will now become clear from a review of the following detailed description of illustrative embodiments, the accompanying drawings, and the claims.

BRIEF DESCRIPTION OF THE DRAWINGS

The drawings disclose illustrative embodiments. They do not set forth all embodiments. Other embodiments may be used in addition or instead. Details that may be apparent or unnecessary may be omitted to save space or for more effective illustration. Conversely, some embodiments may be practiced without all of the details that are disclosed. When the same numeral appears in different drawings, it refers to the same or like components or steps.

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIG. 6A and FIGS. 6B1-6B2 is a diagram showing side (FIG. 6A) and section views (FIGS. 6B1-6B2) of a further example of a capacitive manometer assembly including a diaphragm, baffle, and electrode structure including a guard structure, in accordance with the present disclosure;

Figure 1A:
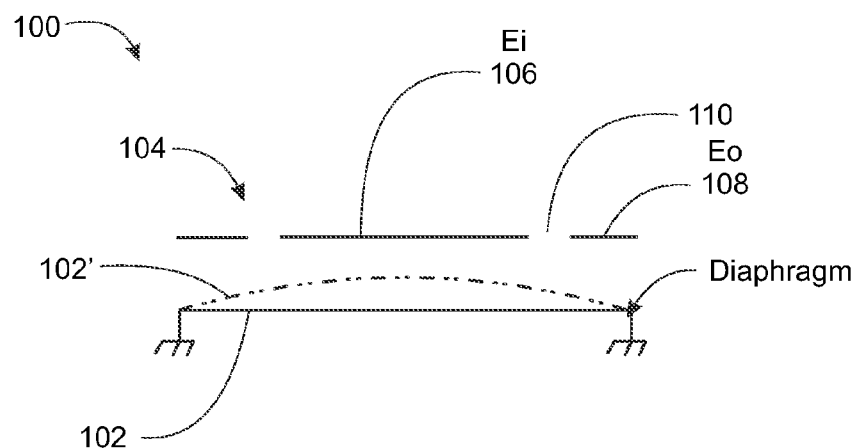
FIGS. 1A-B show a side view (FIG. 1A) and top view (FIG. 1B) of a portion of a prior art capacitance manometer.

While certain embodiments are depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION

Aspects of the present disclosure are directed to apparatus, systems, methods, and techniques, including computer software program products, that can facilitate the provision, operation, and/or control of capacitance manometers having improved precision and/or robustness for pressure measurements.

As is described in detail below and with respect to the accompanying drawings, aspects of the present disclosure address the previously noted problems by providing baffle and/or electrode structures that can reduce and/or block the measurement of transient diaphragm deformation in or for a capacitance manometer due to effects other than pressure, e.g., such as those arising from interaction with one or more reactive gases.

Figure 4A:
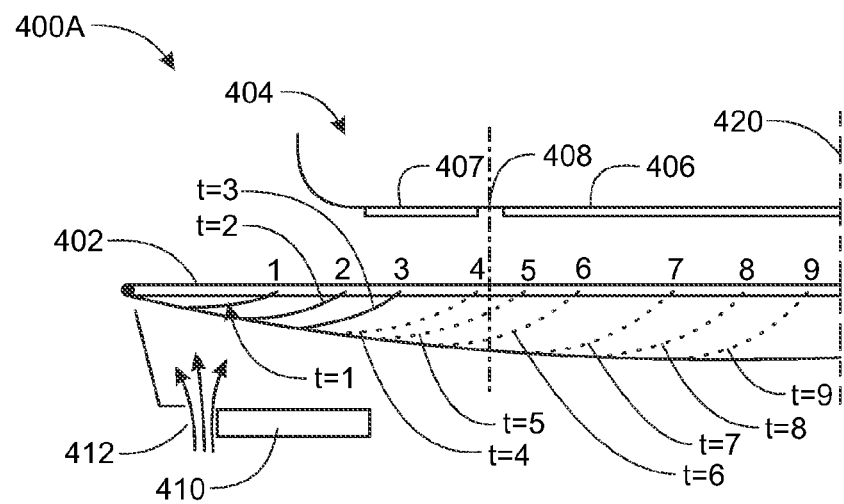
FIGS. 4A-B show two views, including an electrode structure and diaphragm of a prior art capacitance manometer, depicting transient deformation of the diaphragm at different times (FIG. 4A), and a graph of the related measurement error (FIG. 4B)
Figure 4B:
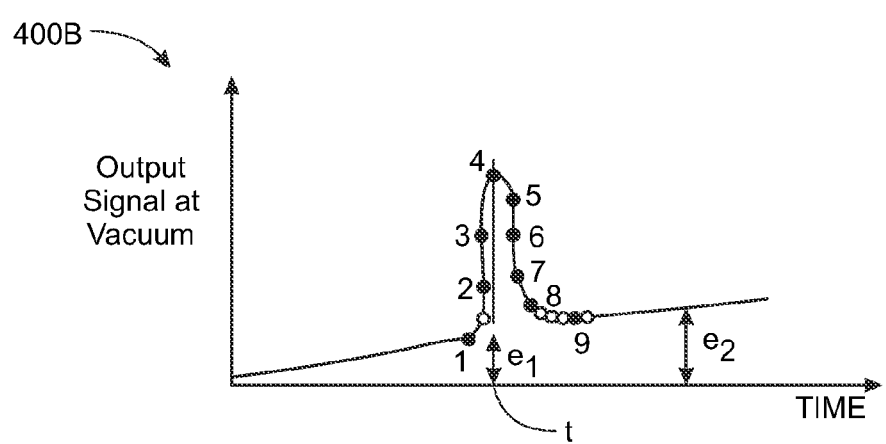

FIGS. 4A-B show two views, including an electrode structure and diaphragm of a capacitance manometer, depicting transient deformation of the diaphragm at different times (FIG. 4A), and a graph of the related measurement error (FIG. 4B). In FIG. 4A, a diaphragm 402 is shown positioned between an electrode structure 404 and a baffle 410. Electrode structure 404 includes an inner electrode 406 and an outer electrode 407 disposed on a planar surface and separated by a gap 408. Centerline 420 is indicated. The baffle 410 has or is adjacent to a slot or orifice 412 that is configured to admit gas to the region adjacent to the diaphragm 402. As shown, orifice 412 is located near the outer radial periphery of the diaphragm 402. The other features of the manometer, e.g., housing, inlet, etc., are omitted in the drawing.

In operation, as a reactive gas is admitted through the orifice 412 and to the region adjacent to the diaphragm 402, the surface of the diaphragm adjacent to the orifice 412 can experience varying degrees of deformation over time, as shown for times t=1 through t=9. Such surface deformation can be caused by the diffusion of reactive gas into the surface of the diaphragm. Examples of such a reactive gas include but are not limited to molecular or atomic fluorine, sulfur hexafluoride, and gas mixtures including such gases. Of course other reactive gases can cause such deformation over time for a manometer diaphragm and the present disclosure is intended to address any or all of such reactive gases. As shown in view A, the surface deformation can spread over the surface of the diaphragm, eventually reaching a steady-state condition.

With continued reference to FIG. 4, FIG. 4B shows the corresponding zero-error reading after each reactive gas exposure and subsequent evacuation to high vacuum (low pressure) indicated for times t=1 through t=9 for the manometer shown in view A. The output signals are shown for a state of vacuum. Two different values of zero-error are indicated, $e_1$ and $e_2$.

As shown in FIGS. 4A-B, when the diaphragm of a capacitance manometer is exposed to a reactive gas or gasses, gas molecules can diffuse into the molecular structure of the diaphragm. Such diffusion can change the tension of the surface (e.g., outer 50 to 100 Angstroms) of the diaphragm in the area where the gas has been introduced. This can cause bending of the diaphragm, which in turn can affect the capacitance measured by the electrodes of the manometer. As a result, this change in capacitance can appear as a pressure change. This deflection may be a transient problem, appearing during the time the gas is initially introduced to, and diffusing into, the diaphragm. Once the gas has diffused into the outer portion of the diaphragm, further diffusion does not take place. Also, when the gas is diffused across the entire diaphragm surface, the surface develops a constant tension, returning to a more uniform shape, e.g., approaching flat, at zero pressure. This process related transient measurement error can adversely affect operations for which the manometer is used, e.g., etch processes and physical vapor deposition as used for semiconductor device fabrication, etc.

As a way to compensate for this transient problem described above, an aspect of the present disclosure provides for a guard structure for the electrode structure of a capacitance manometer. The guard structure (or simply, "guard") can present one or more areas that is/are relatively insensitive to the diffusion of the gas into the diaphragm; so that the resulting changing curvature of the diaphragm with subsequent localized change in the electrode gap (due to the changing surface tension) is not measured or is measured to a lesser degree, thus providing increased or optimal stability of the zero reading and/or pressure reading of the manometer. The guard structure may also provide electrostatic isolation of the two or more electrodes.

As another (or additional) way to compensate for the previously-noted transient problem, another aspect of the present disclosure provides for the introduction of one or more reactive gases to a capacitance manometer, through an area or areas of a baffle, e.g., baffle slot(s), configured in a desired location or locations with respect to the associated electrode structure of the manometer. For example, a baffle slot or slots can be configured to introduce gas to a region or regions of the manometer diaphragm that is/are adjacent to (or directly over) a corresponding guarded zone or zones between guard structures and/or the inner and outer capacitive electrodes, so that the error-inducing effects of positive and negative bending are neutralized or minimized. A guarded zone may be an area of an electrode structure formed by a gap or spacing between guard structures and/or electrodes. For further example, a baffle slot or slots can be configured to introduce gas to a region or regions of the manometer diaphragm that is/are adjacent to (or directly over) one or more electrodes or one or more guards of an electrode structure of the manometer. The peak diaphragm curvature, directly under or adjacent the baffle slot(s), is believed to be attained shortly after t=0, and then as time goes on, the diaphragm surface approaches uniform saturation; then the diaphragm is "seasoned." As stated above, when the entire surface of the diaphragm is saturated there is no longer a transient problem. The particular pattern of the area where the gas is introduced can be influenced by the geometry of the gas inlet. For example, a gas inlet coming in through a tube in the center of a sensor may be used with one configuration of electrode structure, while another electrode geometry may be advantageously used for another inlet geometry.

Figure 5:
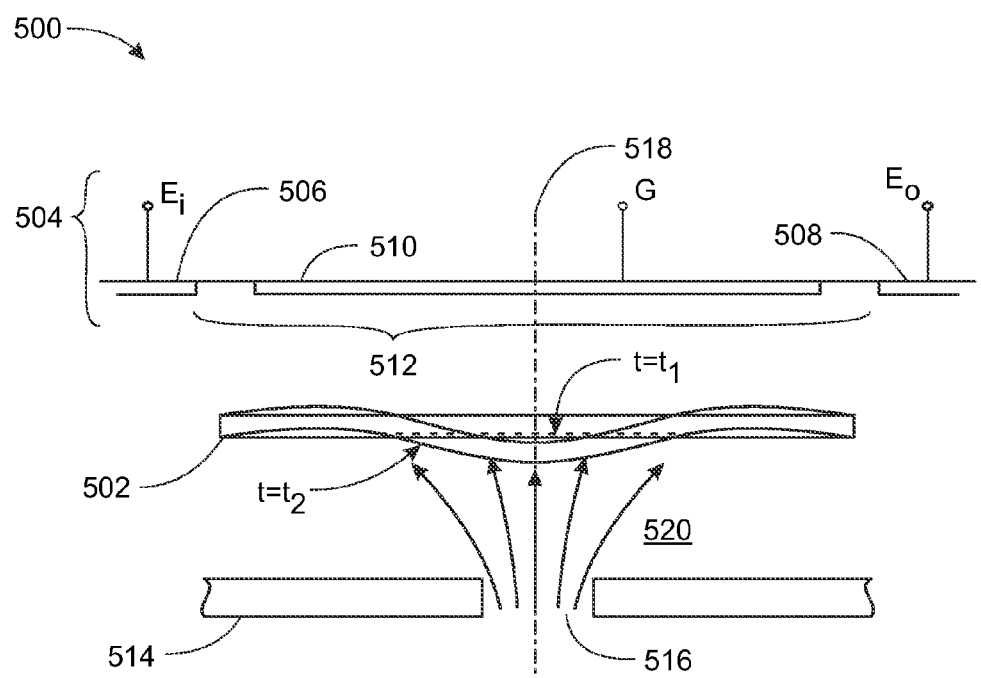
FIG. 5 is a diagram showing a side view of an example of a portion of a capacitive manometer assembly including a diaphragm, baffle, and electrode structure including a guard structure, in accordance with the present disclosure.

FIG. 5 is a diagram showing a portion of capacitance manometer (or capacitance manometer assembly) 500 with a detailed view of a diaphragm, a baffle, and an electrode structure having a guard structure, in accordance with the present disclosure. The device 500 includes a diaphragm 502 located between an electrode structure 504 and a baffle 514. The baffle 514 has one or more apertures 516 to allow gas to the region adjacent the diaphragm 502, as shown. The electrode structure 504 includes an inner electrode 506 and an outer electrode 508. In use, the diaphragm 502 forms a common electrode for the inner and outer electrodes (which can effectively form inner and outer capacitors). The diaphragm may use specific or dedicated structure for use as the common electrode for some embodiments. The electrodes and/or diaphragm can be electrically connected as part of a circuit (not shown), e.g., forming a bridge suitable for capacitance measurements based on deflection of the diaphragm 502. Any suitable conductive material may be used for the electrodes, e.g., copper, silver, compositions including such, or the like. Located between the inner electrode 506 and the outer electrode 508 is a guard structure or guard 510, e.g., as shown within gap 512. The capacitance manometer assembly 500 can also include a support structure (not shown) arranged so as to support the diaphragm 502 so that the diaphragm 502 (more specifically, the perimeter of the diaphragm 502) is constrained relative to the electrode structure 504. While one baffle is shown for manometer 500, two or more baffles may be used in some embodiments.

The guard 510 forms a zone or region of the electrode structure that separates the inner 506 and outer 508 electrodes and does not contribute to capacitance measurements. The guard 510 and aperture 516 can be configured such that the guard 510 and aperture 516 are generally centered and opposed with respect to one another. A diaphragm as shown and described herein can be made of any suitable material. In exemplary embodiments, a so-called superalloy may be used. Examples include, but are not limited to, Hastelloy, Inconel, Waspaloy, Rene alloys (e.g., Rene 41, Rene 80, Rene 95, Rene 104), Haynes alloys, Incoloy, MP98T, TMS alloys, and CMSX single crystal alloys. In some other embodiments, a suitable stainless steel alloy, Alumina, or palladium glass may be used, e.g., on a reference side of a diaphragm. Simplified electrical connections are shown for ease of comprehension.

Various benefits may be afforded by the structural configuration depicted in FIG. 5. For example, by increasing the distance between the inner electrode 506 and the outer electrode 508, the pressure sensitivity of the manometer 500 can be increased. For further example, by the guard 510 presenting an inactive area, with respect to capacitance measurement, the device effectively disregards most if not all of the error that would otherwise be introduced by the transient deformation of the diaphragm in the region adjacent the aperture 516 (i.e., the area of the diaphragm that first receives the incoming gas). Since the initial peak transient is shielded by the guard 510 and over time the change in electrode gap spacing is generally balanced by the inner and outer electrodes, 506 and 508, measurement errors can be mitigated. Of course, while a guard 510 is shown in FIG. 5, in alternate embodiments, guard 510 may be omitted, with aperture 516 generally or precisely centered with gap 512.

FIG. 6A and FIGS. 6B1-6B2 are diagrams showing a side view (FIG. 6A) and section views (FIGS. 6B1-6B2) of a portion of a capacitance manometer 600 including a diaphragm, baffle, and electrode structure with guard structure, in accordance with the present disclosure. The device 600 includes a housing 601 with a diaphragm 602 spaced apart from an electrode structure 604. The electrode structure 604 includes an inner electrode 606 and an outer electrode 608 separated by a guard 610. The structures can have a circular configuration as shown. The housing 601 can be constructed from any suitable material, and is configured to admit a gas flow 616 by way of an inlet 618, as shown, for admitting gas to the region adjacent the diaphragm 602. The housing 601 can also include or provide a support structure arranged so as to support the diaphragm 602 so that the perimeter of the diaphragm 602 is constrained relative to the electrode structure 604. A baffle 612 is present to control entry of the gas to the region adjacent the diaphragm 602. The baffle 612 includes one or more apertures 614 that are strategically located in relation to the guard 610. For example, the midline of the aperture(s) 614 can be centered (or, more or less so) with the midline of the guard 610. As described previously, this configuration can facilitate reduced measurement error due to transient surface deformations of the diaphragm 602.

Figure 1B:
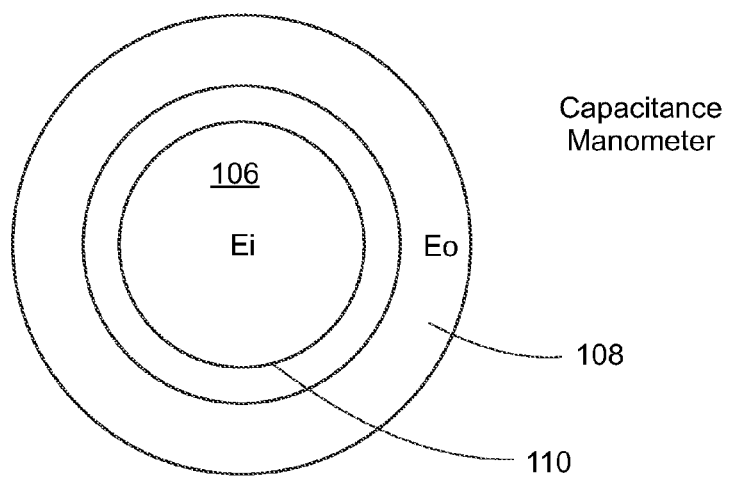
Figure 2A:
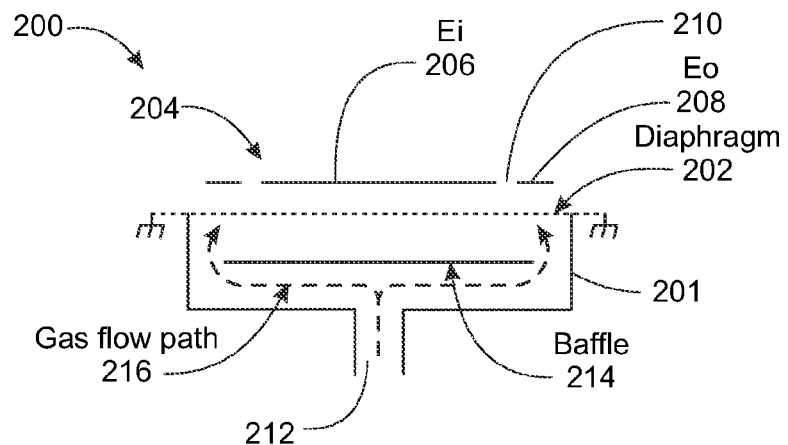
FIGS. 2A-B show a side view (FIG. 2A) and a section view (FIG. 2B) of a portion of another prior art capacitance monometer.
Figure 2B:
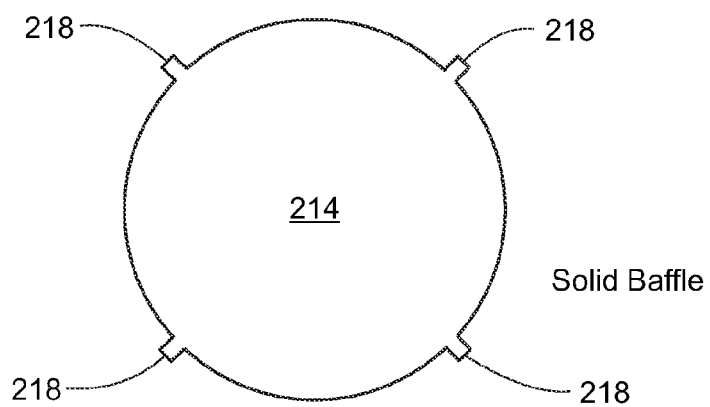
Figure 3A:
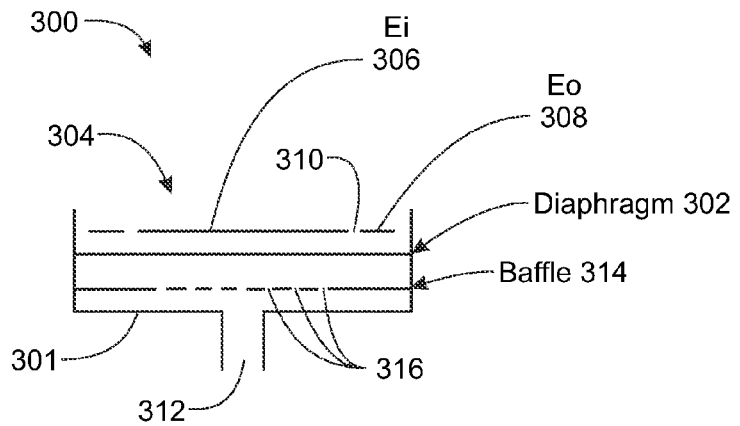
FIGS. 3A-C show a side (FIG. 3A) and alternate section views (FIGS. 3B-C) of a portion of a further prior art capacitance monometer.
Figure 3B:
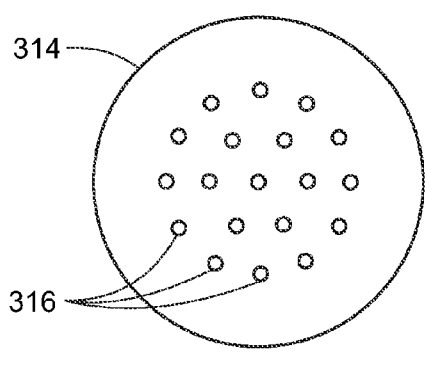
Figure 3C:
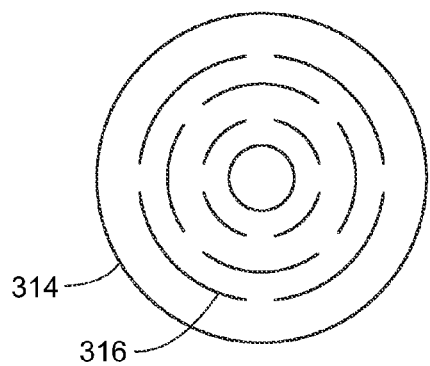

As illustrated in FIG. 6A, Section A-A shows the capacitive sensor 600 with the relatively wide area of the guard 610 between the two electrodes 606 and 608. In FIG. 6B1, section B-B shows the baffle 612 having a ring of slots for allowing gas into the area over the guard 610, while in FIG. 6B2, section B-B shows the baffle 612 having a ring of circular apertures 614 for allowing gas into the area over the guard 610.

Figure 7A:
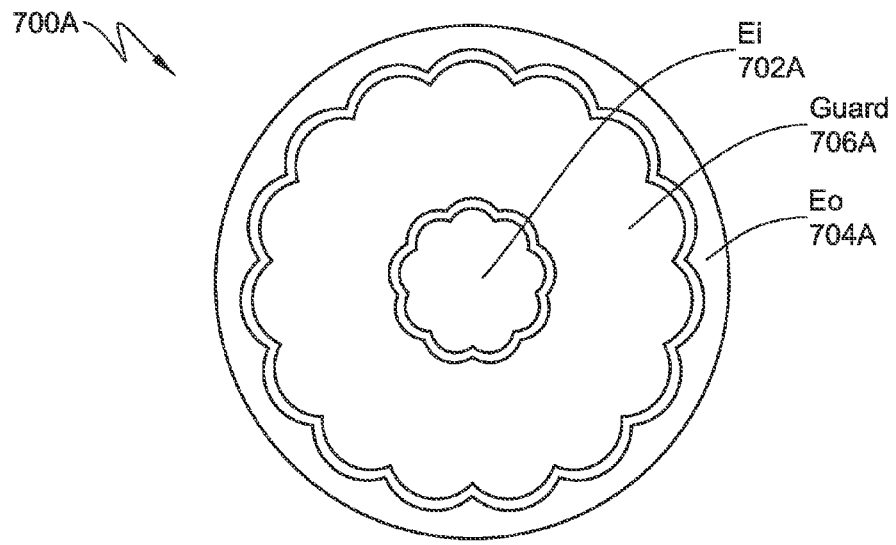
FIG. 7A is a diagrammatic top view of an example of an electrode and guard structure for a capacitance manometer, in accordance with the present disclosure.

While previous examples have depicted the electrodes and guard structures as being circular, these structures may have other shapes, e.g., ones with serrated or linear features and/or may have curved features of desired configuration. FIG. 7A is a diagrammatic top view of an electrode and guard structure 700A having smooth serrated features for a capacitance manometer, in accordance with the present disclosure. The electrode structure 700A can include an inner electrode 702A and an outer electrode 704A, between which is located a guard 706A. The perimeter of the inner electrode 702A can be selected as desired, e.g., one having smooth serrated perimeter, as shown. The inner perimeter of the guard 706A may be configured in a complementary manner, as shown. The inner perimeter of the outer electrode 704A and outer perimeter of the guard 706A may optionally be configured in a like manner. In exemplary embodiments, the outer electrode 704A can have smooth serrated features or it can have a serpentine shape to increase the radial width (or distance) over which capacitance measurements are made; such shapes can facilitate balancing the respective times between the inner and outer electrodes during which each experiences changes in capacitance due to the changes in diaphragm curvature and deflection.

Figure 7B:
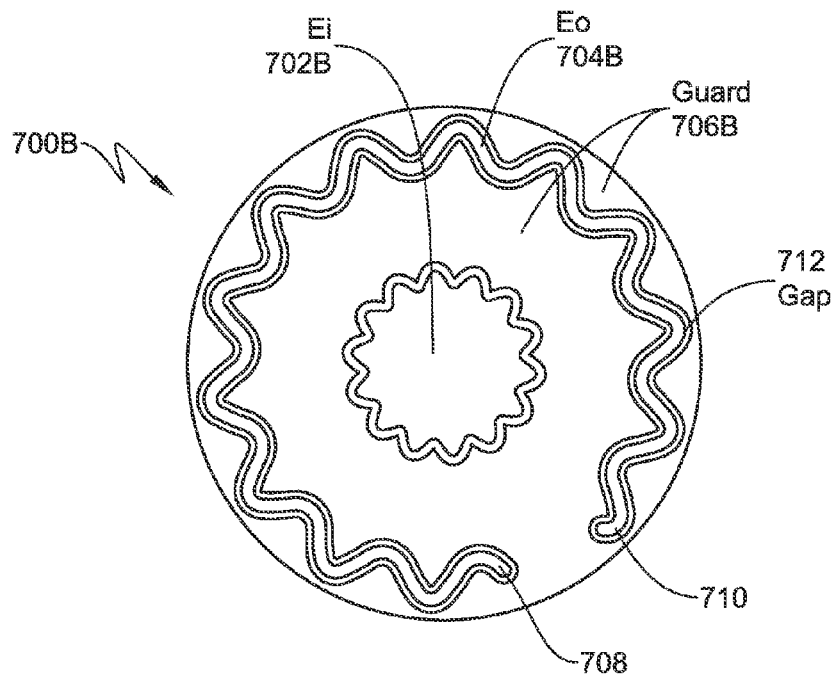
FIG. 7B is a diagrammatic top view of an electrode and guard structure for a capacitance manometer, in accordance with an exemplary embodiment of the present disclosure.

Other examples, similar to that of FIG. 7A, may include the use of desired shapes or contours, e.g., smooth flowing lines, at the perimeters of the conductors, e.g., an outer electrode with a serpentine shape. and the region between the inner and outer electrodes as well as locations, e.g., a guard, radially outside the outer electrode. FIG. 7B is a diagrammatic top view of an example of an electrode and guard structure 700B having smooth flowing features for a capacitance manometer (or manometer assembly), in accordance with the present disclosure. The electrode structure 700B can include an inner electrode 702B and an outer electrode 704B, between which is located a guard 706B. The perimeter of the inner electrode 702B can be selected or designed as desired, e.g., one having smooth flowing perimeter, as shown. The inner perimeter of the guard 706B may be (but is not necessarily) configured in a complementary manner, as shown. The inner perimeter of the outer electrode 704B and outer perimeter of the guard 706B may optionally be configured in a like manner. As is shown, the outer electrode 704B can include or have a non-continuous electrode shape having a first end and a second end, with the first end and second end being separate. The outer electrode 704B can be separated from surrounding or adjacent structure(s), e.g., guards 706B, by a gap 712.

Figure 8:
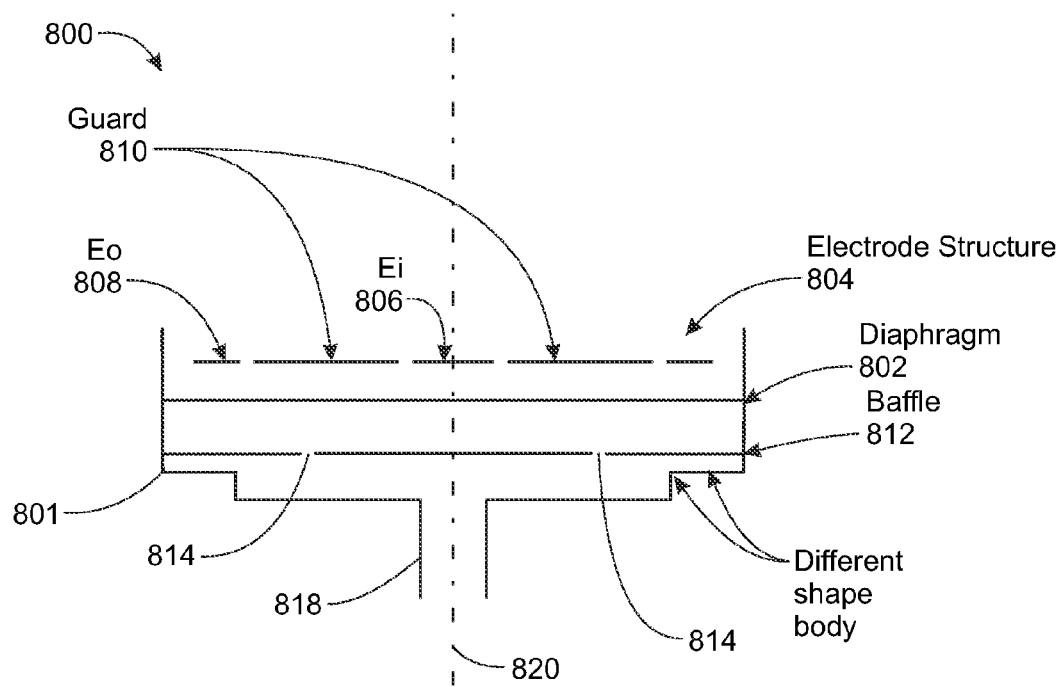
FIG. 8 is a diagrammatic side view of a further example of an electrode and guard structure for a capacitance manometer, in accordance with the present disclosure.

FIG. 8 is a diagrammatic side view of a further example of an electrode and guard structure for a capacitance manometer 800, in accordance with the present disclosure. Capacitance manometer 800 is similar to the device shown in FIGS. 6A and 6B1-6B2 and includes a housing 801 (with a different shape than shown in FIGS. 6A and 6B1-6B2) with a diaphragm 802 spaced apart from an electrode structure 804. The electrode structure 804 includes an inner electrode 806 and an outer electrode 808 separated by a guard 810. The structures can have a circular configuration as shown. The housing 801 is configured to admit a gas flow by way of an inlet 818, as shown, for admitting gas to the region adjacent the diaphragm 802. A baffle 812 is present to control entry of the gas to the region adjacent the diaphragm 802. The baffle 812 includes one or more apertures 814 that are strategically located in relation to the guard 810. For example, the midline of the aperture(s) 814 can be centered (or, more or less so) with the midline of the guard 810. As can be seen in FIG. 8, the internal wall shape can be an important factor or influence on gas flow into the diaphragm portion of a manometer, particularly since the gas may be in molecular flow (where gas molecules are more likely to hit the wall than hit each other).

Figure 9A:
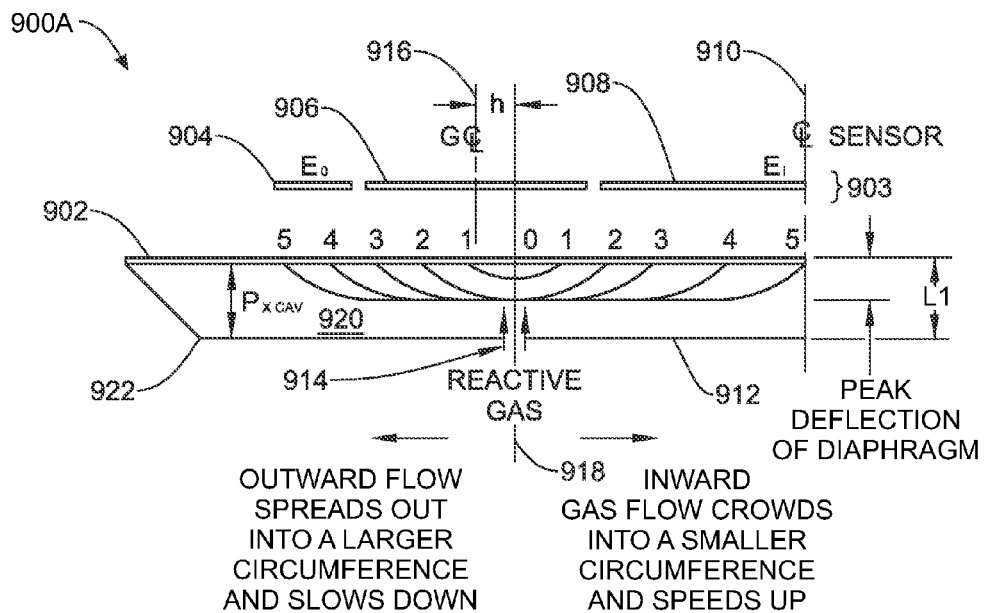
FIGS. 9A-9B show two views of an electrode structure and diaphragm of a capacitance manometer assembly in accordance with the present disclosure, depicting transient deformation of a diaphragm at different times.
Figure 9B:
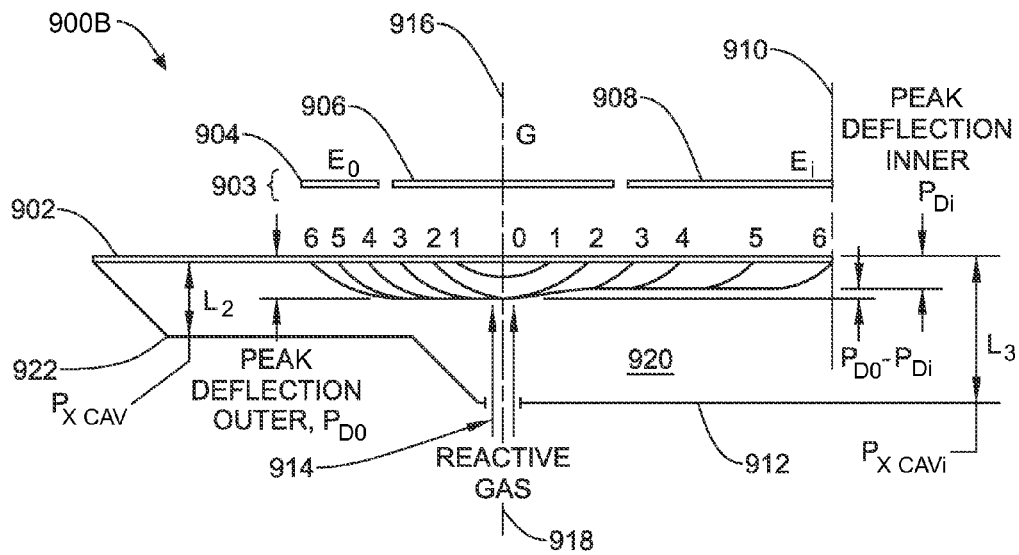

FIGS. 9A-9B show two views of an electrode structure and diaphragm of a capacitance manometer assembly 900A-B in accordance with the present disclosure, depicting transient deformation of a diaphragm at different times; in FIG. 9A, assembly 900A is depicted as experiencing a first succession of time-dependent profiles (1-5) of diaphragm deformation arising from introduction of reactive gas, while in FIG. 9B, a second succession of time-dependent profiles (1-6) are shown. In both FIGS. 9A-9B, the manometer assembly 900A-B includes a diaphragm 902 spaced apart along a longitudinal (or alignment) axis from an electrode structure 903 including an outer electrode 904, a guard 906, and an inner electrode 908. The diaphragm can act as a common electrode for the outer and inner electrodes 904 and 908. The manometer assembly 900A-B can have radial symmetry with respect to a centerline 910, as shown. A baffle 912 can be used for the assemblies and can include one or more inlets or apertures 914 for admitting gas into a pressure cavity ("Px") 920 that is defined in part by a pressure cavity body 922 (which can include the baffle 912). The capacitance manometer assembly can also include a support structure (not shown) arranged so as to support the diaphragm 902 so that the diaphragm 902 is constrained relative to the electrode structure 903. As shown in FIG. 9A, the pressure cavity body 922 can be configured to present a plenum or pressure cavity 920 that is a uniform depth (indicated by L1) across the diaphragm 902. In other instances, the pressure cavity body 922 can be configured to present a plenum or pressure cavity 920 that varies, with a non-uniform depth-(indicated by L2 and L3) across the diaphragm 902, e.g., as shown in FIG. 9B. Of course while one non-uniform depth is indicated in FIG. 9B (i.e., a stepped profile), other configurations may be used within the scope of the present disclosure, e.g., having a desired linear slope, a desired exponential profile, or any other desired profile.

As shown in FIG. 9A, while the baffle apertures 914 may be generally centered, e.g., with respect to a centerline 916 of a guard 906, the baffle apertures 914 can be located inward or outward of the guard centerline 916 (e.g., within a middle third, or other location of the guard) in order to manipulate the timing of the changes in curvature and deflection of the diaphragm 902 and capacitance change between the inner and outer electrodes 904 and 908. A representative displacement, "h," of the aperture centerline 918 is shown in FIG. 9A. In FIG. 9B, the centerline of the guard 916 is shown as being coincident with aperture centerline 918.

As shown in FIG. 9B, the shape of the Px cavity body 922 can be designed as desired, e.g., with a wall profile that changes over a radial distance from centerline 910, to speed or slow down the reactive gas flow and, thus, manipulate the curvature and deflection of the diaphragm. Reactive gas flowing radially outward from the aperture(s) 914 in the baffle 912 passes through a narrowing channel (a taper is shown but other geometry may be used) formed in the Px cavity and then into the narrow channel (indicated by Pxcav o) which concentrates the reactive gas creating greater curvature and deflection of the diaphragm 902, and at the same time slows down the reactive gas flow. Reactive gas flowing radially inward spreads out into a deeper plenum (indicated by Pxcav i) and speeds up, reducing the concentration of reactive gas at the diaphragm surface, reducing the induced changes in curvature and deflection of the diaphragm. This speed of the reactive gas in the radial direction relative to plenum or pressure chamber height (e.g., thin vs. deep channels) occurs in this way, it is believed, because, for very small gaps, the reactive gas is substantially "gettered" (or absorbed/adsorbed) by the metal surfaces as it flows in the radial direction. Gas molecules travel in the cavity at the speed of sound for their particular molecular weight and temperature. The reactive gas molecules may undergo more collisions with the walls in the general vicinity of the "adsorption wavefront" than they do at greater distances beyond this wavefront, and this consumes the reactive gas as it is adsorbed and then diffused into the metal surfaces. This essentially creates an effective speed for the radial flow of reactive gas in the cavity. For a deep plenum there may be many more molecules that travel past the wavefront and strike the walls further radially along the walls and also in more of a parallel direction with the walls. When there is a mixture of non-reactive and reactive gasses, the non-reactive gasses are not "gettered" at the wavefront and travel along the cavity much faster. These effects arising from the shape of the pressure cavity 920 can be used to manipulate the overall timing and deflection of the diaphragm 902 and reduce and/or mitigate effects other than pressure on the output of the manometer sensor 900A-B. In addition, the surface finish or surface chemistry of the body walls may also be modified to influence the flow of gas in and around the baffle(s) and diaphragm.

Figure 10:
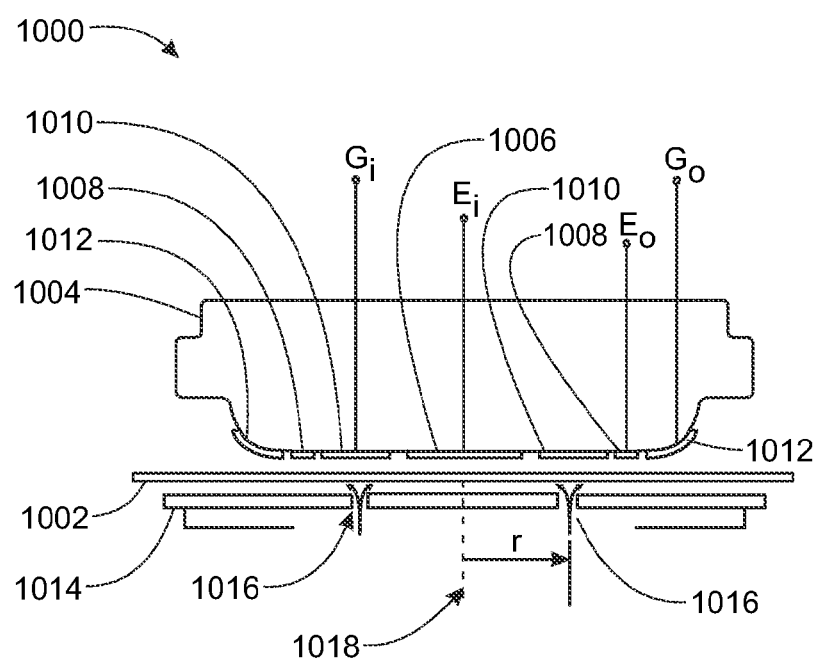
FIG. 10 is a diagrammatic side view of another example of an electrode and guard structure for a capacitance manometer, in accordance with the present disclosure.

FIG. 10 is a diagrammatic side view of another example of an electrode and guard structure 1000 for a capacitance manometer, in accordance with the present disclosure. The electrode structure 1000 is similar to that shown in FIG. 5 but includes an additional guard. The device structure includes a diaphragm 1002 located between an electrode structure 1004 and a baffle 1014. The baffle 1014 has one or more apertures 1016 to allow gas to the region adjacent the diaphragm 1002, as shown. The electrode structure 1004 includes an inner electrode 1006 and an outer electrode 1008. Located between the inner electrode 1006 and the outer electrode 1008 is a first or inner guard 1010. The inner guard 1010 forms a zone or region of the electrode structure that separates the inner 1006 and outer 1008 electrodes and does not contribute to capacitance measurements. The inner guard 1010 and aperture 1016 can be configured such that the inner guard 1010 and aperture 1016 are generally centered and opposed with respect to one another, e.g., as shown in relation to radius, r. As shown, a second or outer guard can also be present 1012 to further mitigate measurement error. Simplified electrical connections are shown for ease of comprehension.

The embodiment shown in FIG. 10 may have particular advantage for use in applications where the electrode voltages are in phase. For such applications, the guard voltage can precisely follow the electrode voltage.

Figure 11:
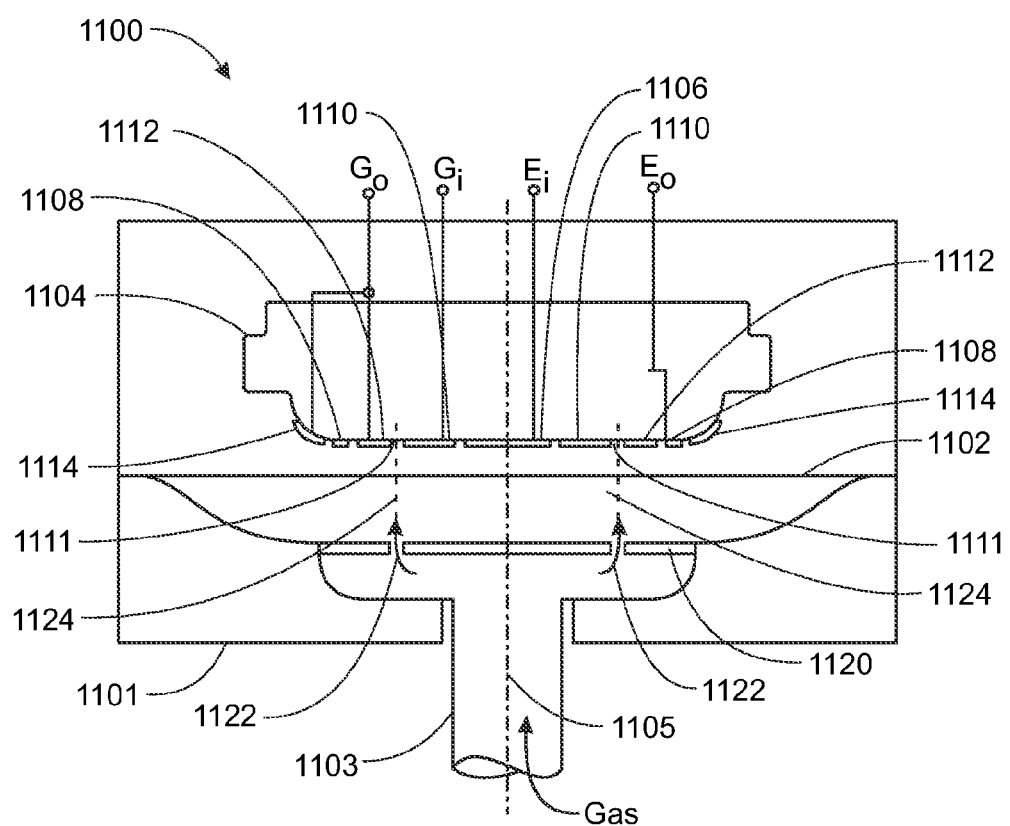
FIG. 11 is a diagrammatic side view of a further example of an electrode and guard structure for a capacitance manometer, in accordance with the present disclosure.

FIG. 11 is a diagrammatic side view of a further example of an electrode and guard structure for a capacitance manometer 1100, in accordance with the present disclosure. Capacitance manometer 1000 includes a housing 1101 including a diaphragm 1102, an inlet 1103, and an electrode and guard structure 1104 for measuring pressure of gas admitted to the device. The electrode and guard structure 1104 includes an inner electrode 1106 and an outer electrode 1108 that are separated by two guards, an inner guard 1110 and an outer guard 1112, on a surface of structure 1104. The inner guard 1110 and outer guard 1112 are separated by one or more gaps 1111. A peripheral guard is also present 1114. Baffle 1120 has one or more apertures 1122 at desired strategic locations. Simplified electrical connections are shown for ease of comprehension.

As shown in FIG. 11, for the electrode and guard structure 1104, the gap(s) 1111 between the inner guard 1110 and outer guard 1112 can be aligned along (or more or less so) the midline(s) 1124 of aperture(s) 1122. As a result the electrode and guard structure 1104 is similar to as shown and described for FIG. 10 except that the inner guard is split into two guards.

The embodiment shown in FIG. 11 may have particular advantage for use in applications where the electrode voltages are 180° out of phase, e.g., as in a typical transformer bridge front end. For such applications, the inner guard voltage can precisely follow the inner electrode voltage, while the outer guard voltage can precisely follow the outer electrode voltage.

Figure 12:
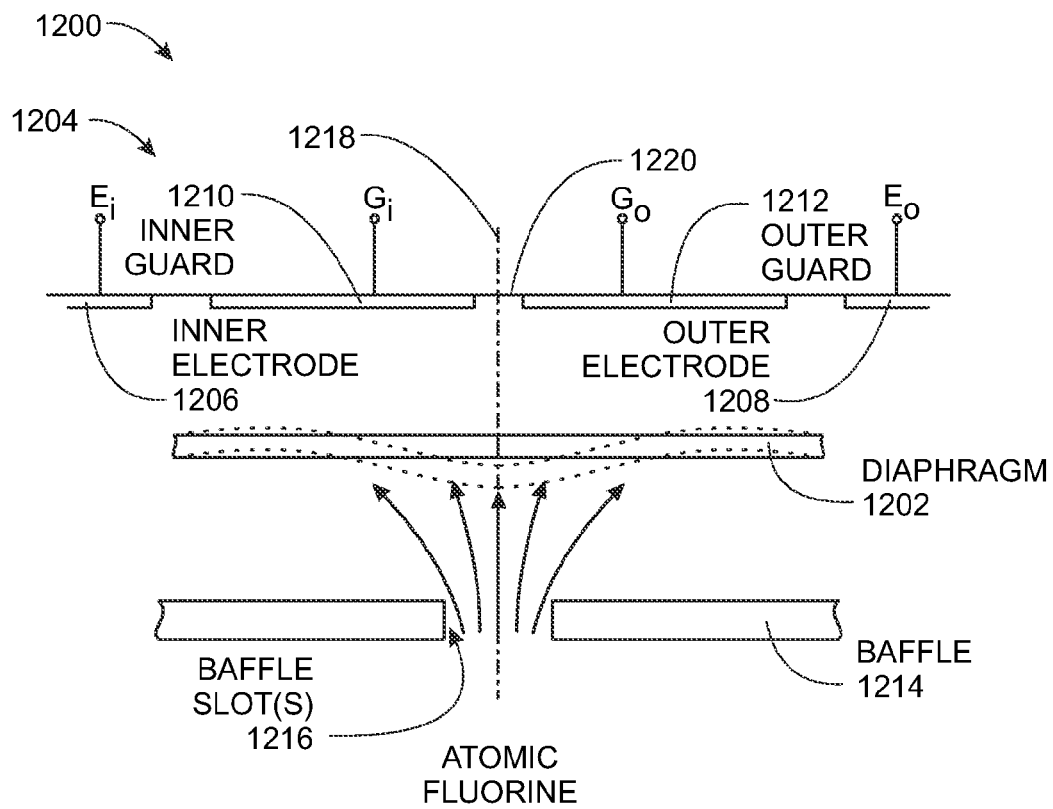
FIG. 12 is a cut out diagrammatic side view of a further example of a capacitance manometer, in accordance with the present disclosure.

FIG. 12 is a detailed side view of a portion of structure 1200 of a capacitance manometer, with a diaphragm undergoing surface deformation, in accordance with the present disclosure. Structure 1200 is similar to that of manometer 1100 of FIG. 11, and includes a diaphragm 1202, an electrode and guard structure 1204, and a baffle 1214 having one or more apertures 1216. The electrode and guard structure 1204 includes an inner electrode 1206 and an outer electrode 1208 separated by an inner guard 1210 and an outer guard 1212. The inner guard 1210 and outer guard 1212 are separated by gap 1220. The gap 1220 between the inner guard 1210 and outer guard 1212 can be aligned along (or, more or less so) the midline 1218 of aperture 1216.

As is shown by the dashed outline of diaphragm 1202, when a reactive gas or gases, e.g., atomic fluorine, is admitted to the manometer structure 1200, the diaphragm can achieve a deformed shape. As described previously, such a deformation may be transient and may subsist over time, reaching a steady state condition. The deformed shape may cause both positive and negative displacement of portions of the diaphragm with respect to the plane (or surface) of the electrode and guard structure 1204. For example, the diaphragm may achieve a surface profile resembling a sinc function or Bessel function of the first kind, as shown. By locating the inner and outer guards and gap 1220 as shown, measurement errors that would otherwise arise from the deformed diaphragm may be mitigated or minimized during operation of the manometer 1200.

The baffle slots can be located directly in the center of the guard rings (or approximately so) in order to concentrate the peak curvature and corresponding axial deflection of the diaphragm at a location where it will not be measured. Exemplary embodiments may utilize only one baffle. A second baffle is not required but two or more baffles may still be used. For exemplary embodiments, a baffle can use a single circumferential slot, or create a small quantity of slots, e.g., 010 in. wide, for instance.

ADVANTAGES

Exemplary embodiments of the present disclosure can provide one or more of the following advantages:

Use of a relatively thick higher tension diaphragm can provide that the membrane bending strain that is induced by the very thin layer of process-modified diaphragm material is resisted by a stiffer element; thus reducing the overall changes in diaphragm curvature.

Reduction of manufacturing cost.

Maximized or increased pressure sensitivity.

Reduction in measurement errors arising from process-modified (induced) diaphragm deformation because of the baffle slotted hole location, which concentrates the peak curvature and corresponding axial deflection of the diaphragm at a location where it will not be measured.

Maintaining adequate base capacitance by use of a smaller electrode gap.

Doing away with a need for the use of traps.

Decreased time constant for the system, which can provide for a quicker system response compared to previous techniques.

EXEMPLARY EMBODIMENTS

An exemplary embodiment of the present disclosure can include a capacitive manometer or capacitive manometer assembly comprising:

(a) a diaphragm including a conductive material and (b) an electrode structure including an inner or center electrode and an outer electrode, wherein the diaphragm is movable relative to the electrode structure between (i) a zero position when the pressure on each side of the diaphragm is the same and (ii) a maximum differential position when the maximum measurable differential pressure is applied to the diaphragm, and a baffle with one or more apertures configured to admit gas to a region adjacent the diaphragm that minimizes effects of surface deformation of the diaphragm due to effects other than pressure.

The one or more apertures in the baffle can be configured in alignment with a gap between the electrodes on the diaphragm.

A superalloy can be used for diaphragm of the manometer.

A further exemplary embodiment of the present disclosure can include a capacitive manometer or capacitive manometer assembly comprising:

(a) a diaphragm including a conductive material and (b) an electrode structure including an inner or center electrode, an outer electrode, and a guard structure disposed between the inner and outer electrodes, wherein the diaphragm is movable relative to the electrode structure between (i) a zero position when the pressure on each side of the diaphragm is the same and (ii) a maximum differential position when the maximum measurable differential pressure is applied to the diaphragm, and (b) a baffle with one or more apertures configured to admit gas to a region adjacent the diaphragm.

The guard structure can include a continuous guard or an inner and an outer guard separated by a gap.

The guard structure can include a third guard disposed on the electrode structure adjacent the outer electrode at a greater radial distance from the center of the electrode structure.

The one or more apertures in the baffle can be configured in alignment with a gap between the electrodes and/or the guard structure on the diaphragm.

A superalloy can be used for diaphragm of the manometer.

The components, steps, processes, methods, structure, features, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, benefits and advantages. These also include embodiments in which the components and/or steps are arranged and/or ordered differently. For example, while embodiments are described herein in the context of dual electrode capacitance manometers, other embodiments of the present disclosure are applicable to single electrode manometers.

Further, while various materials and/or components are described herein, other suitable materials and/or components may of course be used in addition to or substitution for those described.

Moreover, methods, steps, processes, and/or algorithms described herein may be implemented with, in, or by use of suitable computer systems, computer devices, and/or computer processors (e.g., a CPU or graphics processing unit or the like); and, such may implement or utilize a memory unit or storage location, which may be or include an article of manufacture including a non-transitory machine-readable storage medium; and executable program instructions embodied in the machine readable storage medium that when executed by a processor of a programmable computing device configures the programmable computing device to carry out, perform, or control the performance of the methods, steps, processes, and/or algorithms. For example, electrode and diaphragm structures as described herein may be implemented with the assistance of computer-aided drawing software running on a suitable computer system configured alone or with a suitable communication network. For further example, measurement electronics of a capacitance manometer as described herein may be connected to a suitable communication network, e.g., for calibration and/or measurement.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. All articles, patents, patent applications, specifications, and other publications which have been cited or presented in this disclosure are hereby incorporated herein by reference.

What is claimed is:

1. A capacitive manometer assembly comprising:
   a diaphragm including a conductive material;
   an electrode structure including an inner electrode and an outer electrode, wherein the inner electrode and outer electrode are separated from one another, wherein the diaphragm is movable relative to the electrode structure between (i) a zero position when the pressure on each side of the diaphragm is the same and (ii) a maximum differential position when the maximum measurable differential pressure is applied to the diaphragm;
   a support structure arranged so as to support the diaphragm so that the diaphragm is constrained relative to the electrode structure, and the diaphragm is spaced from and axially aligned with the inner and outer electrodes relative to an alignment axis of the manometer;
   a baffle with one or more apertures configured to admit gas to a region adjacent the diaphragm, wherein the baffle is configured to reduce effects of surface deformation of the diaphragm due to reactive gas.

2. The capacitive manometer assembly of claim 1, wherein the one or more apertures in the baffle are configured in alignment, along the alignment axis of the capacitive manometer assembly, with a gap between the inner and outer electrodes on the diaphragm.

3. The capacitive manometer assembly of claim 1, wherein the diaphragm comprises a superalloy.

4. The capacitive manometer assembly of claim 1, further comprising a housing having an inlet for admitting gas, wherein the diaphragm, electrode structure, support structure, and baffle are disposed within the housing.

5. A capacitive manometer assembly comprising:
   a diaphragm including a conductive material;
   an electrode structure including an inner electrode, an outer electrode, and a guard structure disposed between the inner and outer electrodes, wherein the diaphragm is movable relative to the electrode structure between (i) a zero position when the pressure on each side of the diaphragm is the same and (ii) a maximum differential position when the maximum measurable differential pressure is applied to the diaphragm;
   a support structure arranged so as to support the diaphragm so that the diaphragm is constrained relative to the electrode structure, and the diaphragm is spaced from and axially aligned with the inner and outer electrodes relative to an alignment axis of the manometer; and
   a baffle with one or more apertures configured to admit gas to a region adjacent the diaphragm, wherein the baffle is configured to reduce effects of surface deformation of the diaphragm due to reactive gas.

6. The capacitive manometer assembly of claim 5, wherein the guard structure comprises a continuous guard.

7. The capacitive manometer assembly of claim 5, wherein the guard structure comprises an inner and an outer guard separated by a gap.

8. The capacitive manometer assembly of claim 7, wherein the guard structure comprises a third guard disposed on the electrode structure adjacent the outer electrode at a greater radial distance from the center of the electrode structure.

9. The capacitive manometer assembly of claim 5, wherein the one or more apertures in the baffle are configured in alignment, in a directed parallel to the alignment axis of the capacitive manometer assembly, with a gap between the electrodes or one of the electrodes and the guard structure on the diaphragm.

10. The capacitive manometer assembly of claim 5, wherein the diaphragm comprises a superalloy.

11. The capacitive manometer assembly of claim 5, further comprising a housing having an inlet for admitting gas, wherein the diaphragm, electrode structure, support structure, and baffle are disposed within the housing.

12. The capacitive manometer assembly of claim 5, wherein the outer electrode comprises a non-continuous electrode having a first end and a second end, wherein the first end and second end are separate.

13. The capacitive manometer assembly of claim 5, wherein the one or more apertures in the baffle are configured in alignment, in a direction parallel to the alignment axis of the capacitive manometer assembly, with the guard structure on the diaphragm.

14. The capacitive manometer assembly of claim 13, wherein the guard structure comprises an inner and an outer guard separated by a gap.

15. The capacitive manometer assembly of claim 14, wherein the guard structure comprises a third guard disposed on the electrode structure adjacent the outer electrode at a greater radial distance from the center of the electrode structure.

16. The capacitive manometer assembly of claim 13, wherein the one or more apertures in the baffle are aligned, in a direction parallel to a longitudinal axis of the capacitive manometer assembly, with an inner third of the guard structure on the diaphragm, wherein the guard structure is divided into inner, middle, and outer thirds in a radial direction from the center of the electrode structure.

17. A capacitive manometer comprising:
   a housing:
   a diaphragm including a conductive material;
   an electrode structure including an inner electrode and an outer electrode, wherein the inner electrode and outer electrode are separated from one another, wherein the diaphragm is movable relative to the electrode structure between (i) a zero position when the pressure on each side of the diaphragm is the same and (ii) a maximum differential position when the maximum measurable differential pressure is applied to the diaphragm;

a support structure arranged so as to support the diaphragm so that the diaphragm is constrained relative to the electrode structure, and the diaphragm is spaced from and axially aligned with the inner and outer electrodes relative to an alignment axis of the manometer;

a baffle with one or more apertures configured to admit gas to a region adjacent the diaphragm, wherein the baffle is configured to reduce effects of surface deformation of the diaphragm due to reactive gas.

18. The capacitive manometer of claim 17, wherein the electrode structure further comprises a guard structure disposed between the inner and outer electrodes.

19. The capacitive of manometer of claim 18, wherein the guard structure comprises an inner and an outer guard separated by a gap.

* * * * *